United States Patent
Mueller et al.

(10) Patent No.: US 11,583,186 B2
(45) Date of Patent: Feb. 21, 2023

(54) DEVICE FOR DETERMINING INFORMATION RELATING TO A SUSPECTED OCCLUDING OBJECT

(71) Applicant: KONINKLIJKE PHILIPS N.V., Eindhoven (NL)

(72) Inventors: Manfred Mueller, Eindhoven (NL); Arjen Van Der Horst, Tilburg (NL); Gerhardus Wilhelmus Lucassen, Eindhoven (NL); Bernardus Hendrikus Wilhelmus Hendriks, Eindhoven (NL); Charles Frederik Sio, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 327 days.

(21) Appl. No.: 16/480,001

(22) PCT Filed: Jan. 15, 2018

(86) PCT No.: PCT/EP2018/050807
§ 371 (c)(1),
(2) Date: Jul. 23, 2019

(87) PCT Pub. No.: WO2018/137949
PCT Pub. Date: Aug. 2, 2018

(65) Prior Publication Data
US 2019/0365248 A1 Dec. 5, 2019

(30) Foreign Application Priority Data
Jan. 24, 2017 (EP) .................................. 17152770

(51) Int. Cl.
*A61B 5/00* (2006.01)
*A61B 5/1459* (2006.01)
(Continued)

(52) U.S. Cl.
CPC ........ *A61B 5/02007* (2013.01); *A61B 5/0075* (2013.01); *A61B 5/0084* (2013.01); *A61B 5/0261* (2013.01); *A61B 5/1459* (2013.01)

(58) Field of Classification Search
CPC ..... A61B 5/0075; A61B 5/0084; A61B 5/145; A61B 5/14503; A61B 5/14535; A61B 5/1455
See application file for complete search history.

(56) References Cited

U.S. PATENT DOCUMENTS

| 5,839,443 A | 11/1998 | Rose |
| 7,603,166 B2 | 10/2009 | Casscells, III et al. |

(Continued)

FOREIGN PATENT DOCUMENTS

| EP | 2430981 A1 | 3/2012 |
| JP | 2011272787 A | 12/2011 |
| WO | 2015074045 A2 | 5/2015 |

OTHER PUBLICATIONS

Greco, Frank A. "Reflectance Changes in Clotting Native Blood: Evidence of a Red Cell Process." Pathophysiology of haemostasis and thrombosis 36, No. 1 (2007): 23-31.*

(Continued)

*Primary Examiner* — Carolyn A Pehlke

(57) ABSTRACT

The present invention relates to a device for determining information relating to a suspected occluding structure. It is described to provide (210) a spectral resolving unit with at least one broadband radiation. The at least one broadband radiation comprises a first broadband radiation acquired from a region of interest within a vascular structure. An occluding structure is suspected to be located within the region of interest and wherein the first broadband radiation is associated with the suspected occluding structure. At least one spectrally resolved data set is determined (220) on the basis of the at least one broadband radiation, wherein the at (Continued)

least one spectrally resolved data set comprises a first spectrally resolved data set determined on the basis of the first broadband radiation. A processing unit is provided (230) with the at least one spectrally resolved data set on the basis of the at least one broadband radiation. The processing unit determines (240) information relating to the suspected occluding structure, comprising utilisation of the first spectrally resolved data set.

20 Claims, 10 Drawing Sheets

(51) Int. Cl.
*A61B 5/02* (2006.01)
*A61B 5/026* (2006.01)

(56) References Cited

U.S. PATENT DOCUMENTS

| 2003/0032880 | A1 | 2/2003 | Moore |
| 2003/0171741 | A1* | 9/2003 | Ziebol ................. A61B 18/245 606/7 |
| 2004/0024298 | A1* | 2/2004 | Marshik-Geurts ........................... A61B 5/02007 600/326 |
| 2004/0111016 | A1 | 6/2004 | Casscells et al. |
| 2008/0300493 | A1 | 12/2008 | Gatto et al. |
| 2009/0287076 | A1 | 11/2009 | Boyden et al. |
| 2012/0022360 | A1 | 1/2012 | Kemp |
| 2012/0078117 | A1* | 3/2012 | Okada .................... A61B 5/743 600/476 |
| 2014/0111414 | A1 | 4/2014 | Levine |
| 2015/0011896 | A1* | 1/2015 | Yelin .................... A61B 5/0075 600/476 |
| 2015/0248770 | A1 | 9/2015 | Hasegawa |
| 2018/0084982 | A1* | 3/2018 | Yamashita ........... A61B 5/0261 |

OTHER PUBLICATIONS

Nachabe et al: "Estimation of Biological Chromophores Using Diffuse Optical Spectroscopy: Benefit of Extending the UV-VIS Wavelength Range to Include 1000 to 1600 NM"; Optics Exprwess vol. 18, No. 24, Nov. 2010, pp. 1432-1442.

Nachabe et al: "Estimation of Lipid and Water Concentrations in Scattering Media With Diffuse Optical Spectroscopy From 900 to 1600 NM": Journal of Biomedical Optics 15 (3), 017015, May/Jun. 2010, pp. 037015-1-03715-03715-10.

PCT/EO2018050807, ISR & WO, Apr. 18, 2018, 17 Page Document.

Rossow et al: "Lood Flow Measurement and Lot Detection With Near-Infrared Spectroscopy"; Conference Paper, Biomedical Topical Meeting, Jan. 2006, 6 Page Document.

* cited by examiner

DEVICE FOR DETERMINING INFORMATION RELATING TO A SUSPECTED OCCLUDING OBJECT

CROSS-REFERENCE TO PRIOR APPLICATIONS

This application is the U.S. National Phase application under 35 U.S.C. § 371 of International Application No. PCT/EP2018/050807, filed on Jan. 15, 2018, which claims the benefit of European Patent Application No. EP 17152770.8, filed on Jan. 24, 2017. These applications are hereby incorporated by reference herein.

FIELD OF THE INVENTION

The present invention relates to a device for determining information relating to a suspected occluding object, to a system for determining information relating to a suspected occluding object, to a method for determining information relating to a suspected occluding object, as well as to a computer program element and a computer readable medium.

BACKGROUND OF THE INVENTION

The general background of this invention is blood clots, and the providing of information in support of thrombectomy. Thrombectomy, that is the physical removal of blood clots, has been shown to be superior to thrombolysis in treating acute strokes. This has led to a "boom" in thrombectomy devices. Currently there are at least 4 different devices widely available, including the Merci Retriever from Stryker, the Penumbra series of aspiration thrombectomy devices from Penumbra, and the next-generation stent-retrieval devices Trevo Pro and Trevo ProVue from Stryker and Solitaire FR from Covidien. In 2014 in the US alone 13500 thrombectomy procedures were performed with an expected compound annual growth rate of 11%. In about 33% of procedures a second thrombectomy device is used.

However, first time right is critical in thrombectomy, because the time window for treatment is short. Choosing the wrong treatment device can necessitate a second attempt to remove the blood clot, thereby lengthening the procedure time. Each attempt can take 5-10 min. Also choosing the wrong device, necessitating a subsequent different device to be used during the procedure increases costs substantially (average sales price of a thrombectomy device is 4660 US$ in 2014). Also, choosing the wrong device can increase complication rates.

WO2015/074045A2 relates to medical devices, such as catheters, that have imaging and therapeutic agent delivery capabilities. It is described that the therapeutic catheters allow a surgeon to image biological tissues, such as thrombus, prior to delivering therapeutic agents to the tissues, and then re-image the tissue after the procedure to gauge the success of the procedure. It is described that detailed characterization of the biological tissues with, e.g., spectral analysis, is facilitated thereby providing insight into the composition of the tissues and helping to determine the amount of treatment that is appropriate.

US2008/300493A1 describes devices and related methods for detecting blood clots in a blood vessel. An optical microprobe is configured to illuminate a blood vessel with electromagnetic radiation corresponding to the near-infrared portion of the electromagnetic spectrum. The optical microprobe has a pair of fiber optic strands configured for transmission spectroscopy to obtain the absorption spectrum generated by the components within the blood vessel. Because blood clots generate a detectable and unique spectrum, the presence or absence of the blood clot is determined by examining the blood vessel absorption spectrum. A specially-designed holder is configured to stably position the optical microprobe relative to the blood vessel and is used to facilitate precise blood clot detection along a length of blood vessel.

US2004/111016A1 describes methods for the detection of inflammation associated with vulnerable atherosclerotic plaque to prevent heart attack and stroke. The methods are also applicable to detection of infection, cancer, wounds or auto-immune disease in the body. Certain embodiments of the methods provide a way of predicting the level of vulnerability of an atherosclerotic plaque to rupture or thrombus formation by assessing via fiber optic NIR spectrophotometry the status of two or more parameters associated with inflamed atherosclerotic plaque in a vessel of a living patient. From these measurements such conditions as low pH, hypoxia, low glucose, oxidative stress or compounds abundant in vulnerable plaque such as oxidized LDL cholesterol and oxidized metabolites of NO, significant active macrophage population, thin plaque cap, as well as senescence and/or apoptosis of smooth muscle or endothelial cells are determined with the assistance of a suitably programmed microprocessor. By considering together the status of some or all of these conditions with respect to successive sites along a vessel wall, particular plaques which are at significant risk of rupturing or thrombosing can be distinguished from "normal" vessel wall and from "intermediate" and relatively stable or "lower risk" plaques; Sites having more of the indicator conditions would be considered most in need of prompt intervention, and certain combinations of parameter levels would be suggestive of relatively stable plaque. Also described is a multi-parameter catheter and analytical processing assembly for use in the methods.

EP243098A1 relates to a blood vessel inner wall analyzing apparatus provided with a structure for more accurately analyzing components of substances adhered to the inner walls of blood vessels. A blood vessel inner wall analyzing apparatus is provided with illuminating means, detecting means and analyzing means. The illuminating means illuminates a light component in a measurement wavelength range of 1957 nm to 2713 nm onto a measured position from an end surface of a light illuminating fiber inserted into a carotid artery. The detecting means receives a light component from a measured position through an end surface of a light receiving fiber within the carotid artery. The light component to be detected is a light component in a detection wavelength range which extends 15 nm on both short and long sides of the selected center wavelength, with each one or more center wavelengths being selected from a wavelength group comprised of specific wavelengths respectively in the measurement wavelength range. The analyzing means analyzes for the presence or absence of substances differing from blood by using intensity information on the detected light component.

However, there is a continued need to support the neuro interventionalist's choice of the correct thrombectomy device to use in a procedure.

SUMMARY OF THE INVENTION

It would be advantageous to have an improved device for determining information relating to a suspected occluding object, such as a blood clot.

The object of the present invention is solved with the subject matter of the independent claims, wherein further embodiments are incorporated in the dependent claims. It should be noted that the following described aspects and examples of the invention apply also to the device for determining information relating to a suspected occluding object, the system for determining information relating to a suspected occluding object, the method for determining information relating to a suspected occluding object, and for the computer program element and the computer readable medium.

According to a first aspect, there is provided a device for determining information relating to an occluding structure as defined in appended claim 1.

According to a second aspect, there is provided a system for determining information relating to an occluding structure as defined in appended claim 9.

According to a third aspect, there is provided a method for determining information relating to an occluding structure as defined in appended claim 10.

According to a first example, there is provided a device for determining information relating to a suspected occluding structure, comprising:

an input unit;
a spectral resolving unit; and
a processing unit.

The input unit is configured to provide the spectral resolving unit with at least one broadband radiation. The at least one broadband radiation comprises a first broadband radiation acquired from a region of interest within a vascular structure. An occluding structure is suspected to be located within the region of interest and wherein the first broadband radiation is associated with the suspected occluding structure. The spectral resolving unit is configured to provide the processing unit with at least one spectrally resolved data set on the basis of the at least one broadband radiation, wherein the at least one spectrally resolved data set comprises a first spectrally resolved data set determined on the basis of the first broadband radiation. The processing unit is configured to determine information relating to the suspected occluding structure, wherein the determination of the information relating to the suspected occluding structure comprises utilisation of the first spectrally resolved data set.

In other words, optical spectroscopy is used to provide information relating to a suspected occluding structure, such as blood clots, and determine the location and/or information about composition and/or physical properties of the suspected occluding structure. This can be used to determine if a blood clot is indeed present, and if a blood clot is present can be used to discriminate between different types of blood clots, for example to determine if a blood clot is rich in red blood cells, to determine if a blood clot is rich in Fibrin, and to determine if a blood clot is of a type that resists thrombectomy and will have to be treated by thrombolysis.

In this manner, the correct thrombectomy device to remove the blood clot can be determined, thereby decreasing treatment time, reducing cost, and reducing patient risk by reducing the need to undertake a second blood clot removal procedure if the incorrect type of device was initially chosen.

In an example, the at least one broadband radiation comprises a second broadband radiation acquired from within the vascular structure. The second broadband radiation is not associated with the suspected occluding structure. The at least one spectrally resolved data set comprises a second spectrally resolved data set determined on the basis of the second broadband radiation. The determination of the information relating to the suspected occluding structure then comprises utilisation of the second spectrally resolved data set.

In other words a reference measurement of for example blood can be made, that is used as a base reference to which the measurement of the suspected occluding structure, such as a suspected blood clot, is compared. In this way, the natural occurring variations in blood composition between patients can be accounted for when determining if a blood clot for example is present, and if it is present to provide information on that blood clot. In this manner, a better discriminatory signal is provided.

In an example, the second broadband radiation was acquired from the region of interest.

In other words baseline is acquired from near to the location of the suspected occluding structure, such as the suspected blood clot.

In an example, the suspected occluding structure is a blood clot, and wherein determination of the information relating to the blood clot comprises a differentiation between a first blood clot type that is rich in red blood cells and a second blood clot type that is rich in fibrin.

In this manner, a determination can be made if a blood clot is present, and its location can be determined. Also, if a blood clot is present a Fibrin rich blood clot can be differentiated from a blood clot that is rich in red blood cells, thereby enabling the correct type of thrombectomy device to remove the blood clot to be determined.

In an example, the differentiation between the first blood clot type and the second blood clot type comprises a determination of at least one physiological parameter. The at least one physiological parameter comprises one or more of: amount of haemoglobin; haemoglobin oxygen saturation; an amount of scattering; a vessel packaging parameter; water content; and the amount of at least one haemoglobin derivative.

In other words, on the basis of acquired spectra relating to a blood clot, appropriate analysis of the spectra can be used to determine parameters relating to the blood clot, enabling the type of blood clot to be determined. From the type of blood clot, the appropriate thrombectomy device to remove the blood clot to be determined.

In an example, the determination of the at least one physiological parameter comprises one or more of: a fitting of an optical model to the at least one spectrally resolved data set; application of at least one multivariate analysis tool to the at least one spectrally resolved data set; a partial least squares discriminant analysis of the at least one spectrally resolved data set; application of support vector machines to the at least one spectrally resolved data set; application of a k nearest neighbour analysis; and application of deep learning algorithms to the at least one spectrally resolved data set.

Thus, computational efficient means can be used to determine the type of blood clot, and such means can be continually improved as more data is acquired.

In an example, the differentiation between the first blood clot type and the second blood clot type comprises utilisation of a look-up-table.

In other words, a look-up-table is used to link the parameters to a blood clot type based on which a selection advising on the thrombectomy device to be used can be made.

In an example, the first broadband radiation comprises radiation that was reflected from the blood clot.

Thus an efficient means is provided to analyse and determine the type of blood clot from reflected radiation, obviating the need to push a probe past or into the blood clot. In an example, the second broadband radiation comprises radiation that was reflected from within the vascular structure.

In an example, the at least one broadband radiation comprises radiation in the range 400 nm to 800 nm.

In an example, the information relating to the blood clot comprises one or more of: an evaluation of which thrombectomy device or devices is or are most suitable for removal of the blood clot; an assessment of the physical consistency of the blood clot; an assessment of the density of the blood clot; and an assessment of the fibrin content of the blood clot.

According to a second example, there is provided a system for determining information relating to a suspected occluding structure, comprising:

a radiation source;

at least one optical fibre;

a device for determining information relating to a suspected occluding structure according to the first example and any associated example; and an output unit.

The at least one optical fibre is configured to transfer broadband radiation generated by the radiation source to within the vascular structure. The at least one optical fibre is configured to transfer broadband radiation reflected from within the vascular structure to the device, wherein the radiation transferred to the device comprises the at least one broadband radiation. The output unit is configured to output the information relating to the suspected occluding structure.

According to a third example, there is provided a method for determining information relating to a suspected occluding structure, comprising:

a) providing a spectral resolving unit with at least one broadband radiation, wherein the at least one broadband radiation comprises a first broadband radiation acquired from a region of interest within a vascular structure, wherein an occluding structure is suspected to be located within the region of interest and wherein the first broadband radiation is associated with the suspected occluding structure;

b) determining at least one spectrally resolved data set on the basis of the at least one broadband radiation, wherein the at least one spectrally resolved data set comprises a first spectrally resolved data set determined on the basis of the first broadband radiation;

c) providing a processing unit with the at least one spectrally resolved data set on the basis of the at least one broadband radiation; and d) determining by the processing unit information relating to the suspected occluding structure, comprising utilisation of the first spectrally resolved data set.

In an example, in step a) the at least one broadband radiation comprises a second broadband radiation acquired from within the vascular structure, wherein the second broadband radiation is not associated with the suspected occluding structure; and within step b) the at least one spectrally resolved data set comprises a second spectrally resolved data set determined on the basis of the second broadband radiation; and within step d) the determination of the information relating to the suspected occluding structure comprises utilisation of the second spectrally resolved data set.

According to another aspect, there is provided a computer program element controlling a device and/or system as previously described which, if the computer program element is executed by a processing unit, is adapted to perform the method steps as previously described.

According to another aspect, there is provided a computer readable medium having stored computer element as previously described.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
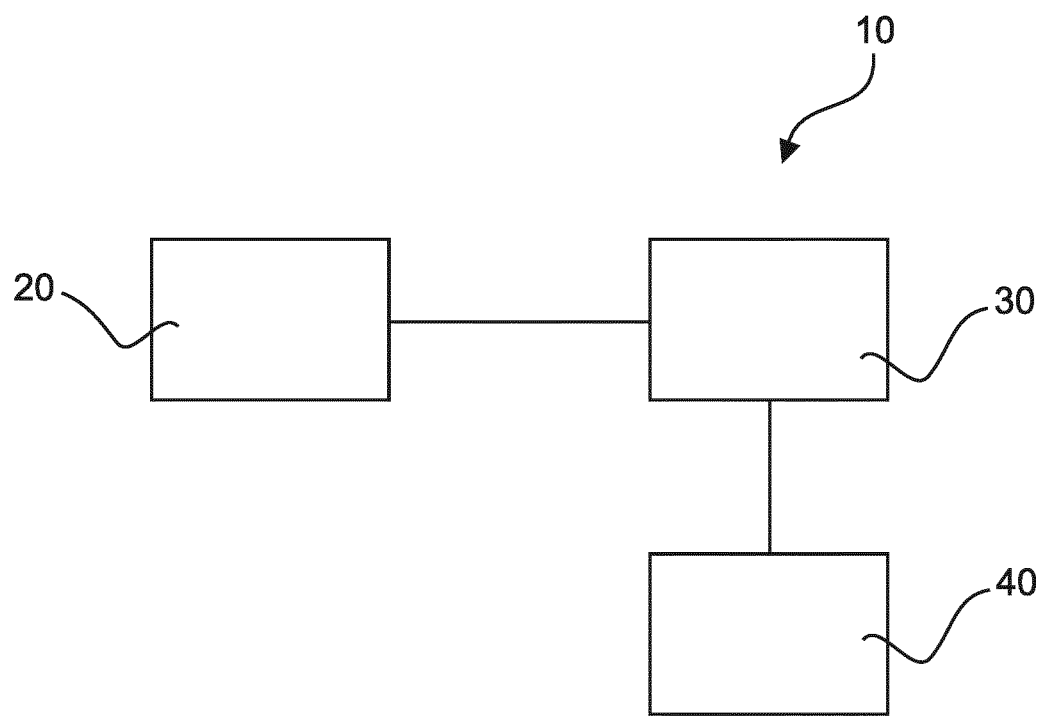
FIG. 1 shows a schematic set up of an example of a device for determining information relating to a suspected occluding object.

FIG. 1 shows an example of a device 10 for determining information relating to a suspected occluding structure. The device 10 comprises an input unit 20, a spectral resolving unit 30, and a processing unit 40. The input unit 20 is configured to provide the spectral resolving unit 30 with at least one broadband radiation. The at least one broadband radiation comprises a first broadband radiation acquired from a region of interest within a vascular structure. An occluding structure is suspected to be located within the region of interest and the first broadband radiation is associated with the suspected occluding structure. The spectral resolving unit 30 is configured to provide the processing unit 40 with at least one spectrally resolved data set on the basis of the at least one broadband radiation. The at least one spectrally resolved data set comprises a first spectrally resolved data set determined on the basis of the first broadband radiation. The processing unit 40 is configured to determine information relating to the suspected occluding structure. The determination of the information relating to the suspected occluding structure comprises utilisation of the first spectrally resolved data set.

In an example, the spectral resolving unit is a spectrometer.

In an example, the device comprises a radiation source. In an example, the radiation source is a tuneable laser. In an example, the spectral resolving unit comprises a tuneable laser cooperating with a radiation detector, such that a broadband radiation comprises the tuneable laser operating over a range of wavelengths and this radiation is detected to provide a spectrally resolved data set.

In an example, the occluding structure is a blood clot. However, the occluding structure could be other than a blood clot, such as a foreign object or a stenosis.

In an example, the device has an output unit.

According to an example, the at least one broadband radiation comprises a second broadband radiation acquired from within the vascular structure. The second broadband radiation is not associated with the suspected occluding structure. The at least one spectrally resolved data set then comprises a second spectrally resolved data set determined on the basis of the second broadband radiation. The determination of the information relating to the suspected occluding structure then comprises utilisation of the second spectrally resolved data set.

In an example, determination of the information relating to the suspected occluding structure, such as a suspected blood clot, comprises utilisation of a ratio between the first and second spectrally resolved data sets.

According to an example, the second broadband radiation was acquired from the region of interest.

According to an example, the suspected occluding structure is a blood clot. The determination of the information relating to the blood clot comprises a differentiation between a first blood clot type that is rich in red blood cells and a second blood clot type that is rich in fibrin.

In an example, the differentiation between a first blood clot type that is rich in red blood cells and a second type of blood clot that is rich in fibrin comprises a determination of the amount of red blood cells present and/or the amount of fibrin present. In other words, graduations between on the one hand a "rich in red blood cell clot" and a "rich in fibrin clot" is provided that takes into account that real blood clots can exist between being a rich in red blood cell clot and a rich in fibrin clot, and could exist as a blood clot half way between the these two. The determination of information relating to the blood clot then provides this graduation in the actual form of the blood clot.

According to an example, the differentiation between the first blood clot type and the second blood clot type comprises a determination of at least one physiological parameter, wherein the at least one physiological parameter comprises one or more of: amount of haemoglobin; haemoglobin oxygen saturation; an amount of scattering; a vessel packaging parameter; water content; and the amount of at least one haemoglobin derivative.

In an example, the at least one haemoglobin derivative comprises methemoglobin.

In an example, the at least one physiological parameters is determined from the at least first broadband radiation by fitting an optical model derived from diffusion theory to the measured spectra. In an example, fitting the spectra to an optical model can include taking into account a wavelength dependent absorption coefficient and a wavelength dependent reduced scattering coefficient. In an example, a double power law can be used to describe the wavelength dependence of the reduced scattering, where a first law corresponds to the contribution of Mie scattering and a second power law corresponds to the contribution of Rayleigh scattering. The reduced scattering $??'_s$ expressed in $cm^{-1}$ as a function of wavelength $\lambda$ can be written as $$\mu'_s = a\left(\rho_{MR}\left(\frac{\lambda}{\lambda_0}\right)^{-b} + (1-\rho_{MR})\left(\frac{\lambda}{\lambda_0}\right)^{-4}\right)$$

Where, $??_0$ is a normalization wavelength, that in an example can be set to 800 nm, and the parameter a corresponds to the reduced scattering amplitude at this exemplar wavelength. The reduced scattering corresponds to the sum of Mie and Rayleigh scattering and $\rho_{MR}$ is defined as the Mie-to-Rayleigh fraction of the scattering. The reduced scattering slope of the Mie scattering is denoted b, and is related to the particle size.

More detail on the determination of the physiological parameters can be found in the following two papers: R. Nachabé, B. H. W. Hendriks, A. E. Desjardins, M. van der Voort, M. B. van der Mark, and H. J. C. M. Sterenborg, "Estimation of lipid and water concentrations in scattering media with diffuse optical spectroscopy from 900 to 1600 nm", J. Biomed. Opt. 15, 037015 (2010); and Rami Nachabé, Benno H. W. Hendriks, Marjolein van der Voort, Adrien E. Desjardins, and Henricus J. C. M. Sterenborg, "Estimation of biological chromophores using diffuse optical spectroscopy: benefit of extending the UV-VIS wavelength range to include 1000 to 1600 nm", Optics Express 18 (2010) p 1432.

According to an example, the determination of the at least one physiological parameter comprises one or more of: a fitting of an optical model to the at least one spectrally resolved data set; application of at least one multivariate analysis tool to the at least one spectrally resolved data set; a partial least squares discriminant analysis of the at least one spectrally resolved data set; application of support vector machines to the at least one spectrally resolved data set; application of a k nearest neighbour analysis; and application of deep learning algorithms to the at least one spectrally resolved data set.

In an example, the at least one multivariate analysis tool comprises principle component analysis (PCA).

According to an example, the differentiation between the first blood clot type and the second blood clot type comprises utilisation of a look-up-table.

According to an example, the first broadband radiation comprises radiation that was reflected from the blood clot.

According to an example, the second broadband radiation comprises radiation that was reflected from within the vascular structure.

According to an example, the at least one broadband radiation comprises radiation in the range 400 nm to 800 nm.

In an example, the at least one broadband radiation comprises radiation in the range 300 nm to 800 nm.

In an example, the at least one broadband radiation comprises radiation in the range 200 nm to 800 nm.

In an example, the at least one broadband radiation comprises white light radiation.

In an example, the at least one broadband radiation comprises UV light radiation.

In an example, the source of broadband radiation comprises a special UV source directed to the detection of fibrin, through the absorption of UV radiation by fibrin. Thus, a source of radiation can actually relate to more than one source that provides the necessary broadband radiation.

According to an example, the information relating to the blood clot comprises one or more of: an evaluation of which thrombectomy device or devices is or are most suitable for removal of the blood clot; an assessment of the physical consistency of the blood clot; an assessment of the density of the blood clot; and an assessment of the fibrin content of the blood clot.

Figure 2:
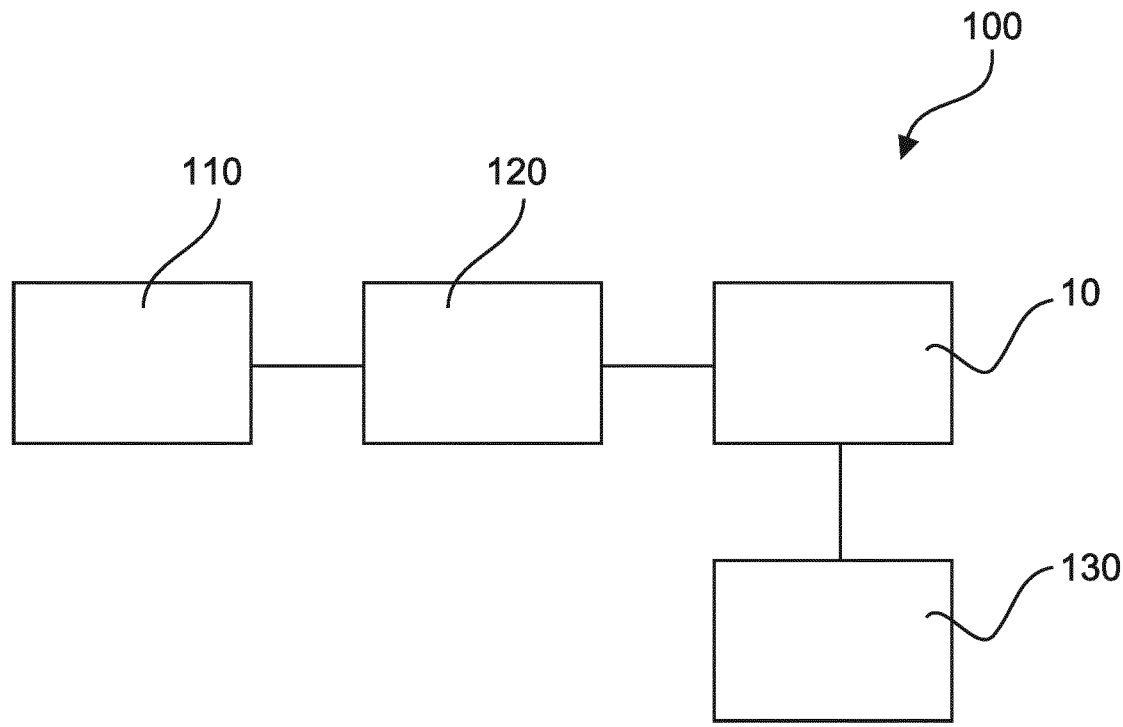
FIG. 2 shows a schematic set up of an example of a system for determining information relating to a suspected occluding object.

FIG. 2 shows an example of a system 100 for determining information relating to a suspected occluding structure. The system comprises a radiation source 110, at least one optical fibre 120, and a device 10 for determining information relating to a suspected occluding structure as described with respect to FIG. 1. The system 100 also comprises an output unit 130. The at least one optical fibre 120 is configured to transfer broadband radiation generated by the radiation source 110 to within the vascular structure. The at least one optical fibre 120 is configured to transfer broadband radiation reflected from within the vascular structure to the device 10. The radiation transferred to the device 10 comprises the at least one broadband radiation. The output unit 130 is configured to output the information relating to the suspected occluding structure.

In an example, the occluding structure is a blood clot.

In an example, one optical fibre is used to transfer radiation to within the patient, and a second optical fibre is used to transfer radiation to the device and the spectral resolving unit. In an example the same optical fibre is used to transfer radiation into and out of the patient.

In an example, the at least one optical fibre is comprised within a Neurology wire with an atraumatic tip.

In an example, the radiation source 110 can form part of the device 10. In an example, the radiation source is a tuneable laser and cooperates with a detector to form the spectral resolving unit 30 of the device 10, from which spectrally resolved data sets can be provided through appropriate operation of the tuneable laser over a range of wavelengths. Thus, the spectral resolving unit can be integrated in or with the radiation source, for example in the case when the radiation source is a tuneable laser.

Figure 3:
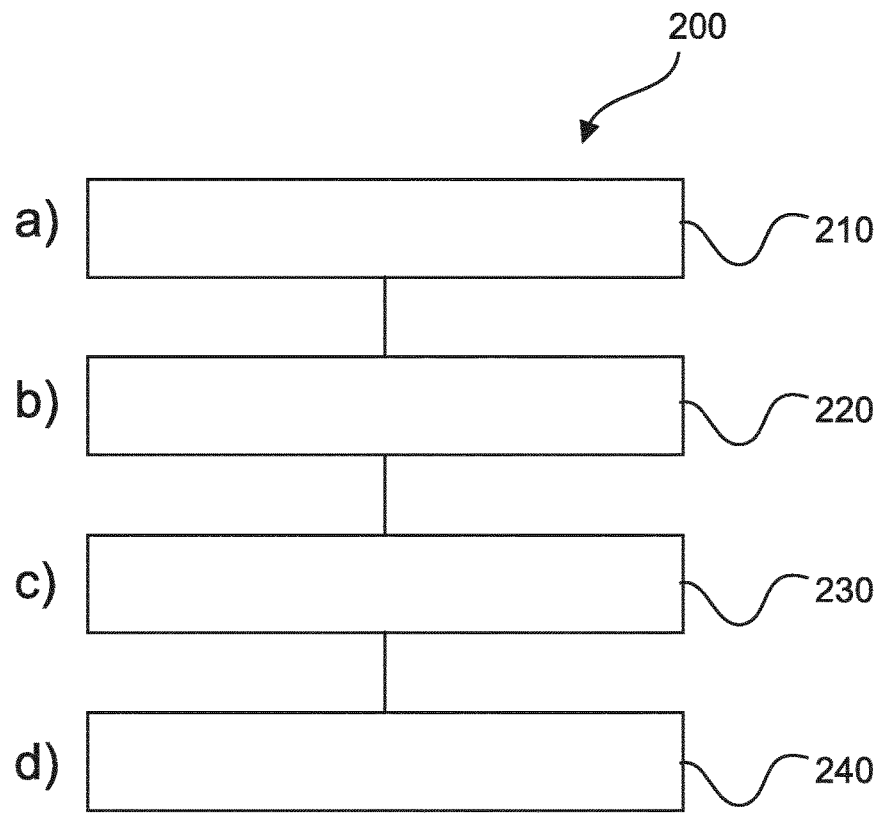
FIG. 3 shows a method for determining information relating to a suspected occluding object.

FIG. 3 shows a method 200 for determining information relating to a suspected occluding structure in its basic steps. The method 200 comprises:

in a providing step 210, also referred to as step a), providing a spectral resolving unit with at least one broadband radiation, wherein the at least one broadband radiation comprises a first broadband radiation acquired from a region of interest within a vascular structure, wherein an occluding structure is suspected to be located within the region of interest and wherein the first broadband radiation is associated with the suspected occluding structure;

in a determining step 220, also referred to as step b), determining at least one spectrally resolved data set on the basis of the at least one broadband radiation, wherein the at least one spectrally resolved data set comprises a first spectrally resolved data set determined on the basis of the first broadband radiation;

in a providing step 230, also referred to as step c), providing a processing unit with the at least one spectrally resolved data set on the basis of the at least one broadband radiation; and in a determining step 240, also referred to as step d), determining by the processing unit information relating to the suspected occluding structure, comprising utilisation of the first spectrally resolved data set.

In an example, the occluding structure is a blood clot.

According to an example, within step a) the at least one broadband radiation comprises a second broadband radiation acquired from within the vascular structure, wherein the second broadband radiation is not associated with the suspected occluding structure; and within step b) the at least one spectrally resolved data set comprises a second spectrally resolved data set determined on the basis of the second broadband radiation; and within step d) the determination of the information relating to the suspected occluding structure comprises utilisation of the second spectrally resolved data set.

In an example, the second broadband radiation is acquired from the region of interest.

In an example, the suspected occluding structure is a blood clot, and wherein determining the information relating to the blood clot comprises differentiating between a first blood clot type that is rich in red blood cells and a second blood clot type that is rich in fibrin.

In an example, differentiating between the first blood clot type and the second blood clot type comprises determining at least one physiological parameter, wherein the at least one physiological parameter comprises one or more of: amount of haemoglobin; haemoglobin oxygen saturation; an amount of scattering; a vessel packaging parameter; water content; and the amount of at least one haemoglobin derivative.

In an example, determining the at least one physiological parameter comprises one or more of: a fitting of an optical model to the at least one spectrally resolved data set; application of at least one multivariate analysis tool to the at least one spectrally resolved data set; a partial least squares discriminant analysis of the at least one spectrally resolved data set; application of support vector machines to the at least one spectrally resolved data set; application of a nearest neighbour analysis; and application of deep learning algorithms to the at least one spectrally resolved data set.

In an example, differentiating between the first blood clot type and the second blood clot type comprises utilisation of a look-up-table.

In an example, the first broadband radiation comprises radiation that was reflected from the blood clot.

In an example, the second broadband radiation comprises radiation that was reflected from within the vascular structure.

In an example, the at least one broadband radiation comprises radiation in the range 400 nm to 800 nm.

In an example, the information relating to the blood clot comprises one or more of: an evaluation of which thrombectomy device or devices is or are most suitable for removal of the blood clot; an assessment of the physical consistency of the blood clot; an assessment of the density of the blood clot; and an assessment of the fibrin content of the blood clot.

The device, system and method for system for determining information relating to a suspected occluding object, such as a suspected blood clot, are now described in more detail in conjunction with FIGS. 4-12.

Figure 4:
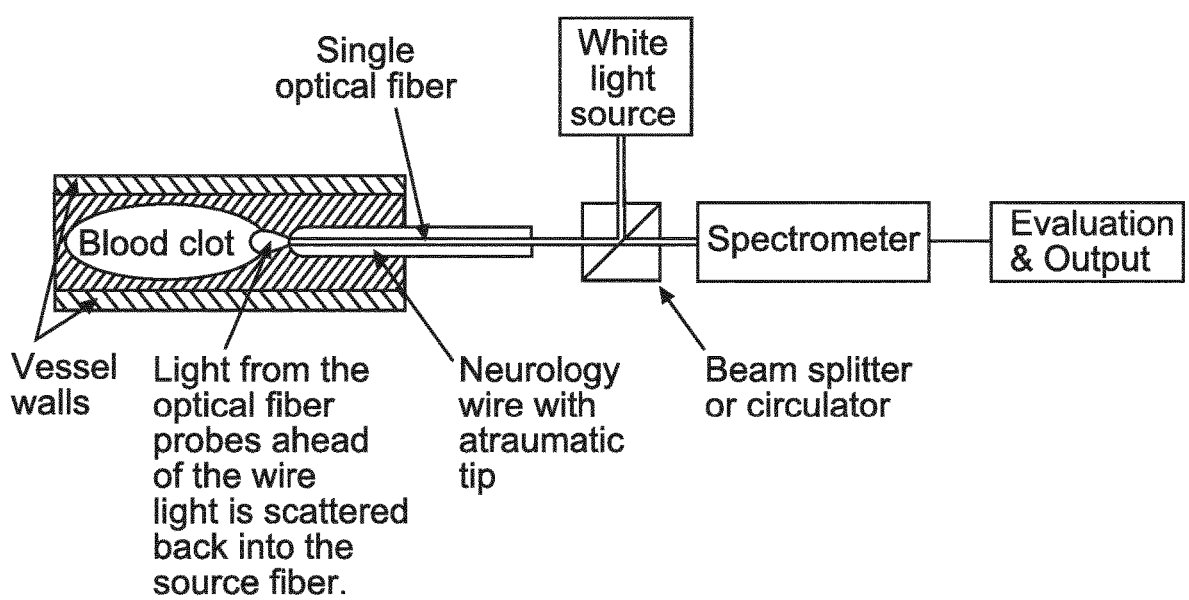
FIG. 4 shows in detail a schematic example of a system for determining information relating to a suspected occluding object.

FIG. 4 shows a detailed example of a system for determining information relating to a suspected occluding object. Thus the system of FIG. 4 is a detailed example of the system 100 shown in FIG. 2. Continuing with FIG. 4, the system consists of a guide wire, a console and an evaluation and output unit, which may be integrated into the console. The console itself is not shown for reasons of clarity, rather the specific elements of the system and the console are discussed. The evaluation part of the evaluation and output unit is an example of the processing unit 40 discussed in relation to the device 10 and system 100 of FIGS. 1 and 2. The output unit of the evaluation and output unit is an example of the output unit 130 discussed in relation to the system 100 of FIG. 2. In FIG. 4, the console has a white light source that emits light with wavelengths covering the spectral range 400 nm to 800 nm. The white light source is an example of the radiation source 110 described with reference to the system of FIG. 2. Continuing with the discussion relating to the system of FIG. 4, the light source can also operate over the wavelength range of 300 nm to 800 nm. In addition, fibrin exhibits spectral features that extend into the ultraviolet range where light absorption by fibrin is high, and as such the light source can operate at wavelengths down to 200 nm. The light source can also operate into the infrared region, up to 2000 nm. The light source can be formed by different emission elements that enables emission over this full range of wavelengths. White light can also refer to an assortment of narrow-band light sources (e.g. a number of LEDs of different wavelengths) or it can refer to a monochromatic tunable light source that is swept over a broad wavelength range or to any combination thereof. Therefore, "white light" here refers to a broad band radiation source that can operate over the above described wavelength ranges extending from 200 nm to 1600 nm. The white light from the light source is coupled into an optical fiber and passed through a neurology guide wire to the tip of that wire. The single optical fibre shown in FIG. 4 is an example of the at least one optical fibre 120 discussed with respect to the system of FIG. 2. In FIG. 4, the guide wire can be inserted into a patient's vascular structure. The light is emitted from the tip of the wire into the blood stream and any clot which is present. The light is partly absorbed and scattered and a part of the light is also scattered back towards the tip, and some of this light is collected back into an optical fiber and transported back into the console. The same optical fibre can be used to emit and collect the light, or different fibres can be used. The light transported back to the console can be considered to be a broadband radiation that is discussed in relation to the system of FIG. 2 that is provided to the device 10. The console can contain optical beam splitters, circulators and/or filters that help in separating the reflected light from the light coming directly from the white light source. In the console the reflected light is guided to a wavelength resolving element that in this example is a spectrometer that determines a wavelength-resolved power spectrum of the reflected light, which forms a spectrally resolved data set. The spectrometer shown in FIG. 4 is an example of the spectral resolving unit 30 of the device 10 that is discussed in relation to FIGS. 1 and 2. It is to be noted that a tuneable laser can be used as the light source, and in this case a wavelength resolving element is not required. A spectrally resolved data set can be formed in different manners, and need not relate to a power spectrum. The guide wire when positioned adjacent to the suspected occluding object, such as a suspected blood clot, as shown in FIG. 4, acquires broadband radiation that relates to the suspected occluding object (e.g., suspected blood clot). By positioning the guide wire away from the suspected occluding object (e.g. blood clot), a broadband radiation measurement of the blood itself, or of the vessel wall or other required background, can be acquired. This can form a baseline against which the spectra from the suspected occluding object (e.g. blood clot) can be referenced. Normal referencing techniques, such as subtracting one spectra from the other or determining the ratio of one spectra to the other, can then be used. However, such a baseline is not necessary but can help to take into account differences in acquired spectra between patients. Thus, it can be determined if there is indeed an occluding object present, and its location can be determined. If there is an occluding object present, it can be determined if it is a blood clot and the type of blood clot present can be determined.

Figure 5:
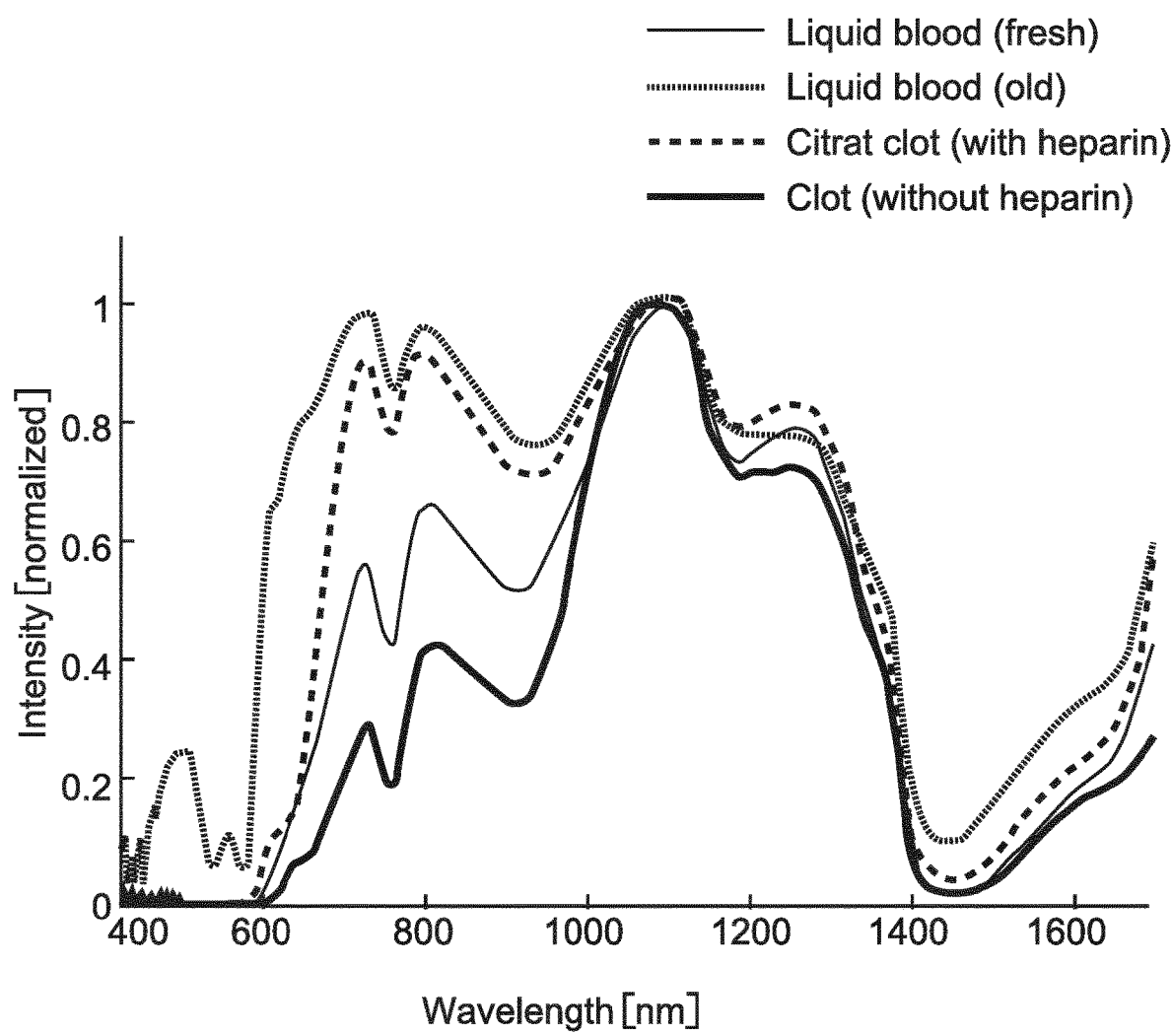
FIG. 5 shows measured diffuse reflection spectra from pig blood, acquired by a system for determining information relating to a blood clot.

FIG. 5 shows example spectra from pig blood and blood clots in pig blood, and as discussed above the wavelength range can extend down to 300 nm or 200 nm if necessary, with the wavelength range only being shown down to 400 nm here for convenience. FIG. 5 shows measured diffuse reflection spectra from pig blood (fresh and about a day old) and of two types of blood clots in the pig clots. The two types of clots are 1) a naturally occurring clot in non-heparinized blood and 2) a citrate induced clot in heparinized blood.

Returning to FIG. 4, and assuming that an occluding object is present in the form of a blood clot, the optical spectra (where here optical can also mean UV and IR as well as visible radiation ranges) is analysed by a processing unit in the evaluation and output unit of the console. This analysis, or evaluation, of the optical spectra and its relationship to the blood clot includes the determination of various physiological parameters that relate to the formation of blood clots. These parameters are: the amount of haemoglobin; haemoglobin oxygen saturation; the amount of scattering; the vessel packaging parameter; water content; and the amount of haemoglobin derivatives such as methemoglobin.

These parameters are determined from the spectra by fitting an optical model derived from diffusion theory to the measured spectra. More detail on this determination can be found in the following two papers by R. Nachabé, B. H. W. Hendriks, A. E. Desjardins, M. van der Voort, M. B. van der Mark, and H. J. C. M. Sterenborg, and by Rami Nachabe, Benno H. W. Hendriks, Marjolein van der Voort, Adrien E. Desjardins, and Henricus J. C. M. referred to above. However, other techniques can be used to determine these parameters such as applying multivariate statistical analysis tools such as PCA, partial least squares discriminant analysis, support vector machines, or deep learning algorithms.

After the parameters have been determined, a classification algorithm of blood clot type (rich in Red Blood Cells "RBC" or rich in fibrin) assigns a blood clot class to the acquired data for that blood clot. This assigning can be based on the estimates of the amount of hemoglobin, oxygen saturation, vessel packaging factor, amount of scattering, water content and amount of hemoglobin derivatives. The result of the determined, or assigned, blood clot class is output on a UI or display of the console, shown as part of the evaluation and output unit of FIG. 4. A look-up-table is used to link the parameters to a clot type. Advice on the thrombectomy device to be used is also presented, in addition to the information relating to the blood clot type.

Thus parameters of interest, and their significance, can be summarized as:

Total hemoglobin concentration: this is higher in clots that are rich in RBCs;

Hemoglobin oxygenation: this is lower in clots than in the surrounding blood because the clots don't participate in the circulation;

Methemoglobin: this is higher in clots because hemoglobin break-down has started;

Vessel radius: this is a substitute, or additional augmenting, parameter for vessel packing;

Scattering parameters: the scattering parameters depend mostly on the particle size. Clots rich in RBCs are basically a lose collection of large particles (RBCs). Therefore, the effective particle size is large. As a result they should have a large Mie fraction and probably also an increased Mie slope. Fibrin rich clots form a more homogenous mass, therefore scattering will mostly happen on smaller inhomogeneities. This results in a smaller Mie fraction and a reduced Mie slope; and Water concentration: this is lower in a clot than in the surrounding blood.

Assigning of Blood Clot Type

Here information determined from acquired spectra are used to differentiate between the blood clots types rich in red blood cells and the blood clots rich in fibrin. Specifically, the spectral evaluation is used to determine estimates of the above described parameters that are used to classify the blood clot type.

There are spectral differences in these blood clots types are because, for example:

A blood clot rich in red blood cells has a higher hematocrit than normal blood. The hematocrit is the ratio of red blood cells to the total plasma volume. The normal range in humans varies between 38 and 43% depending on the gender. With reference to spectra from whole blood with hematocrit in the range 0.38-0.43, an acquired spectra relating to a blood clot can then be compared to such reference spectra from which it can be determined whether or not the blood clot has a higher amount of red blood cells. In particular, by making use of baseline measurements of normal blood during the insertion of the catheter towards the blood clot the hematocrit value of the blood clot elevation compared to normal blood can be detected accurately. This value is important for the characterization of the blood clot, and by using a look-up-table linked to this value a selection advice of the thrombectomy device can be given to the physician.

For a blood clot rich in fibrin the amount of red blood cells is lower than normal full blood. Also, there is a different amount of scattering, due to the fibrin structure of the clot tissue compared to a blood clot rich in red blood cells. The amount of fibrin can also be also detected in the UV wavelength range, where fibrin absorption is high.

Based on the blood clot type, the physician needs to decide on what type of treatment device (for example whether to use Thrombectomy (and which particular device), thrombolysis, or another technique) to use. The processing unit within the evaluation and output unit shown in FIG. 4 provides the physician with a suggestion for this choice. The reason that this is important is because a fibrin rich clot is tough and sticky, and therefore does not deform easily, and can be difficult to remove with conventional stent retrievers of aspiration alone. In contrast, clots rich in red blood cells are soft, friable and slippery which means they may be easier to remove but instead more prone to embolisation into the same or a previously unaffected territory. Therefore, different clot types can require different technologies for the removal. For example, an example of a device that could be suitable for certain fibrin rich clots is the MERCI retriever, whilst for red blood cell rich clots an example of a type device that could be suitable is an aspiration device such as the PENUMBRA. Device that could be suitable for intermediate clots could be standard retrievers like solitaire or TREVO. In addition, or alternatively, an assessment of the physical consistency and/or density of the clot or fibrin content of the clot based on the parameter estimates is displayed to the physician and they can use their expert knowledge to then decide on how to proceed. Such information can in particular be derived from hemoglobin content and scattering determined from the spectra.

The Evaluation and Output unit shown in FIG. 4 can operate in a stand-alone mode, where it can process previously acquired data to determine blood clot type.

The above system can be realised using visible wavelengths, however with respect to clots in the high content of red blood cells, near infrared wavelengths between 1100 nm and 1500 nm can have particular advantages. This is because, high absorption of blood in the blue and green wavelength regions can lead to a reduction in light reflected from the clot, leading to potential difficulties in precise measurement of total haemoglobin concentration. Furthermore, visible light can have a low penetration depth in biological tissue and using infrared light provides for better penetration through the blood clot, which allows for assessment on the inhomogeneous composition. Furthermore, scattering properties that apply in the visible region can be less infrared region. Therefore, the system ideally operates in the visible and near infrared regions.

A system that operates in the near infrared based and visible region, can be as described above with respect to FIG. 4. However, there can be further developments as summarised below. The system thus has:

a guidewire or catheter suitable for use in the human blood vessels that contains at least one optical fiber, that guides white light (that can include light of a wavelength between 1100 nm and 1500 nm) to the tip of the device and reflected light from the tip of the device to a console which contains a spectrally resolving element such a spectrometer, a processing unit that evaluates the spectrum and determines one or more location dependent parameter(s) $P(x)$.

The processing unit carries out classification on features as described above with respect to FIG. 4.

However, the processing unit also runs an algorithm that determines scattering and absorption with respect to unknown absorbers leading to "mystery" absorption peaks, and the processing unit can carry out classification on these features in addition to those features described above with respect to FIG. 4.

The visible and near infrared system is now described in more detail, where specific reference is made to FIGS. 6-12.

Figure 6:
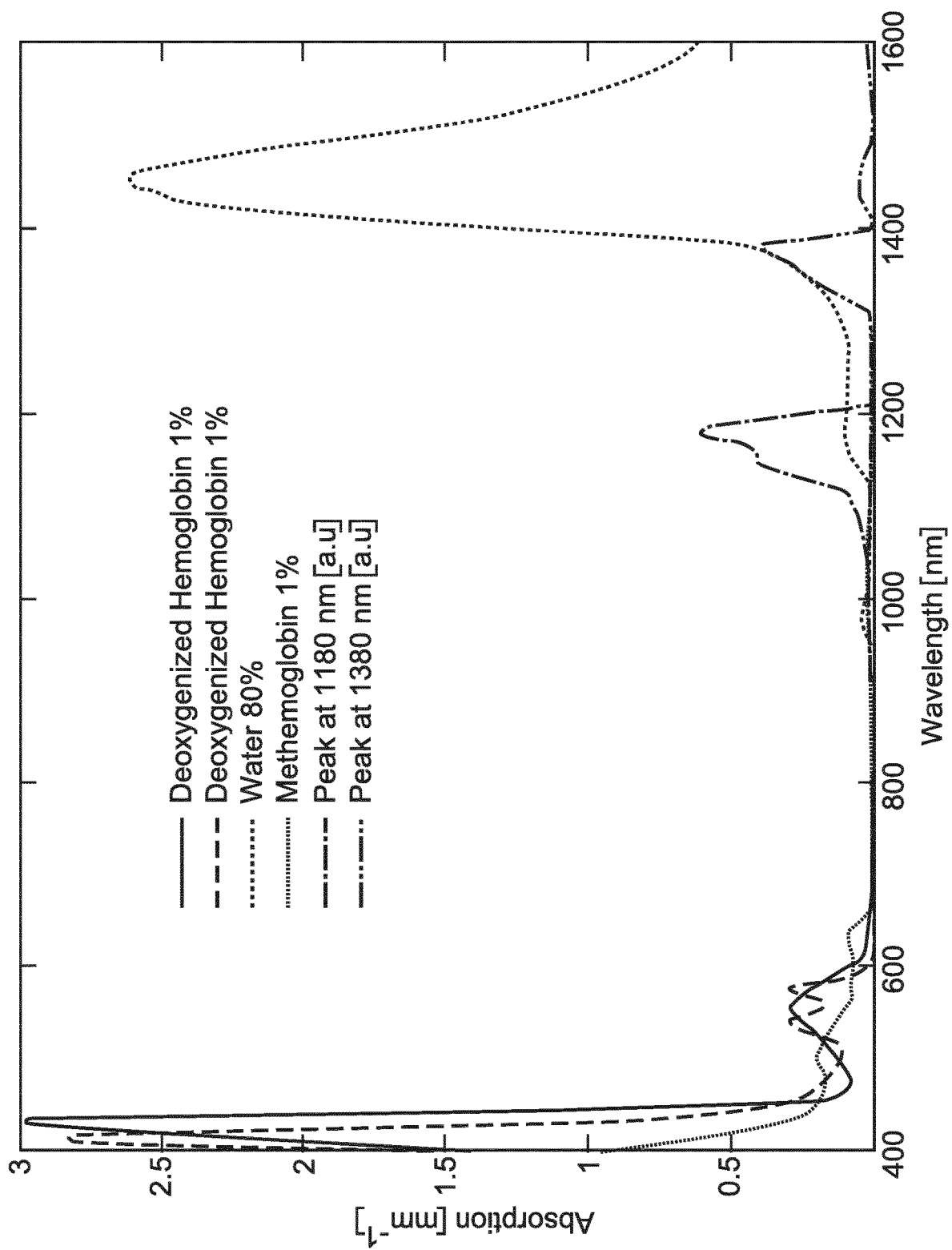
FIG. 6 shows typical absorption curves that are used to fit the measured spectra of blood clots.

FIG. 6 shows typical absorption curves that are used to fit the measured spectra of blood clots. Besides the typical constituents of blood (Oxygenized Hemoglobin, Deoxygenized Hemoglobin, Water and Methemoglobin) it has been found necessary to fit some additional, unidentified absorption peaks at around 1180 nm and 1380 nm.

Figure 7:
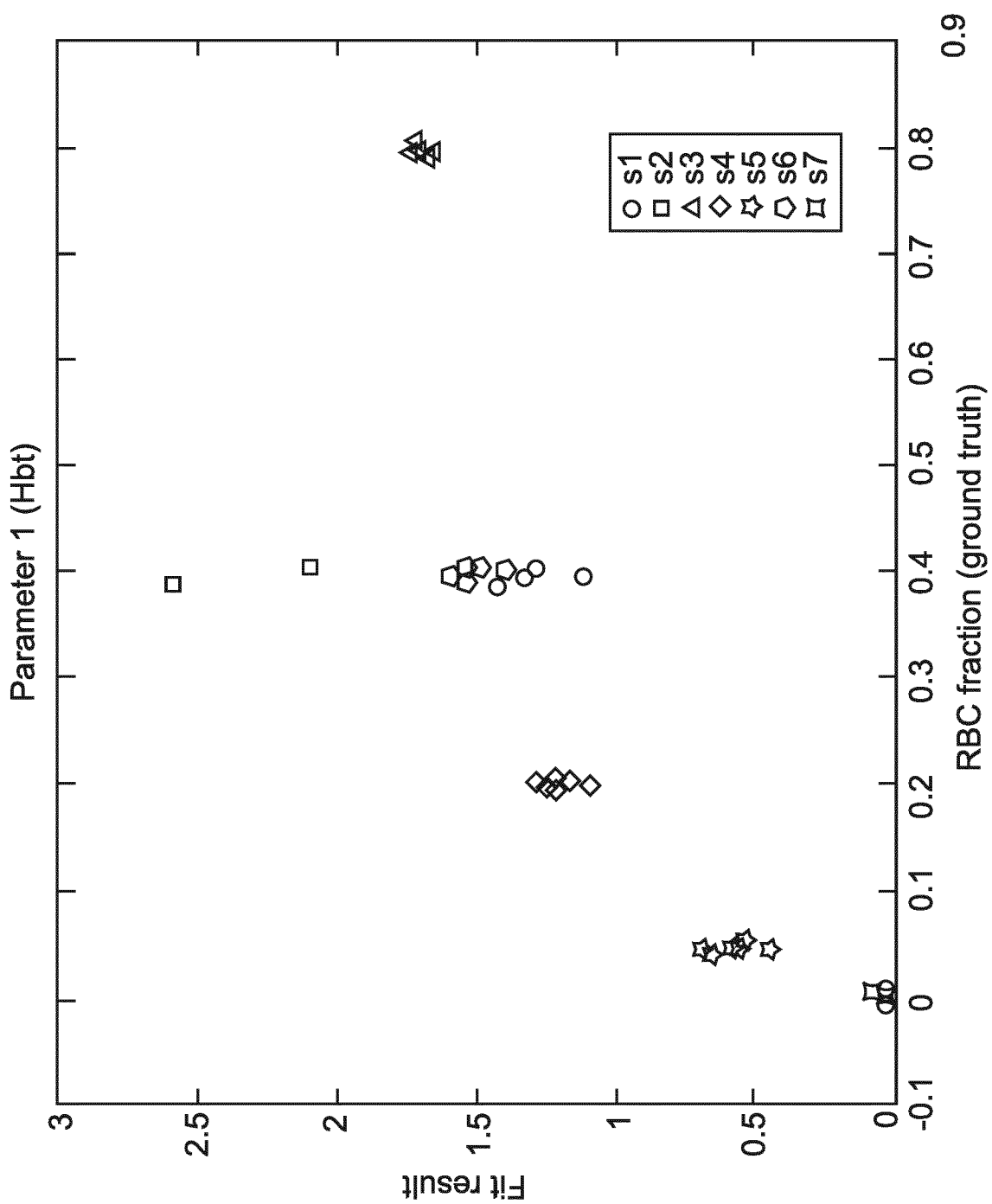
FIGS. 7-11 shows a relationship between the Red Blood Cell concentration in blood clot samples (x-axis) and fitted parameters.

FIG. 7 shows a relationship between the Red Blood Cell concentration in blood clot samples (x-axis) and the fitted total concentration of deoxygenized and oxygenized hemoglobin (y-axis in arbitrary units) for blood clot samples are various composition. Si is an inhomogeneous sample which has areas of higher and lower red blood cell concentration. For low red blood cell fractions this parameter is very distinctive, for higher red blood cell fractions the absorption becomes so high that the fitting algorithm runs into saturation issues and additional parameters might be needed.

Figure 8:
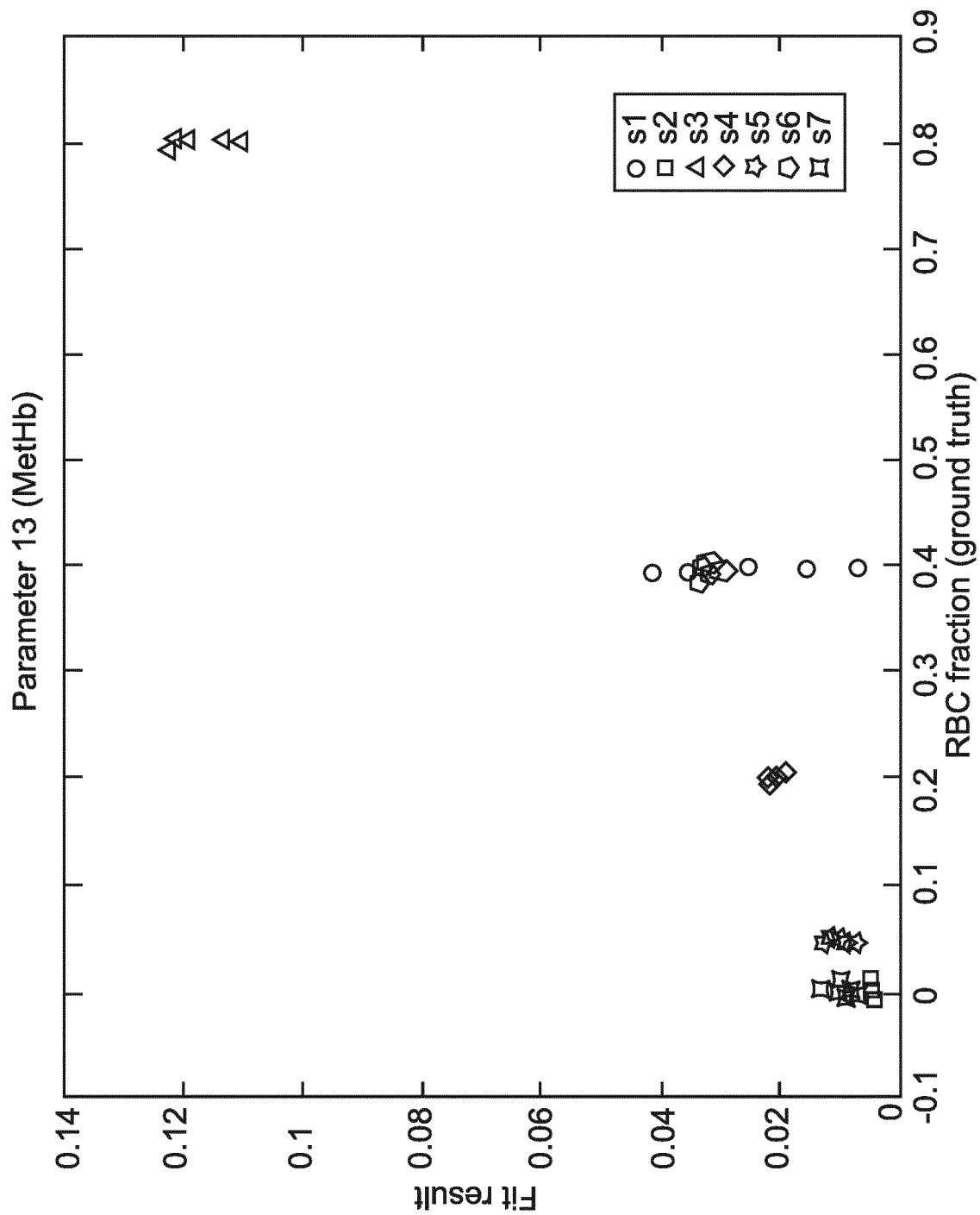

FIG. 8 shows a relationship between the Red Blood Cell concentration in blood clot samples (x-axis) and the fitted concentration of Methemoglobin (y-axis) for blood clot samples of various composition. Si is an inhomogeneous sample which has areas of higher and lower red blood cell concentration. The dependency is nearly linear over the full concentration range.

Figure 9:
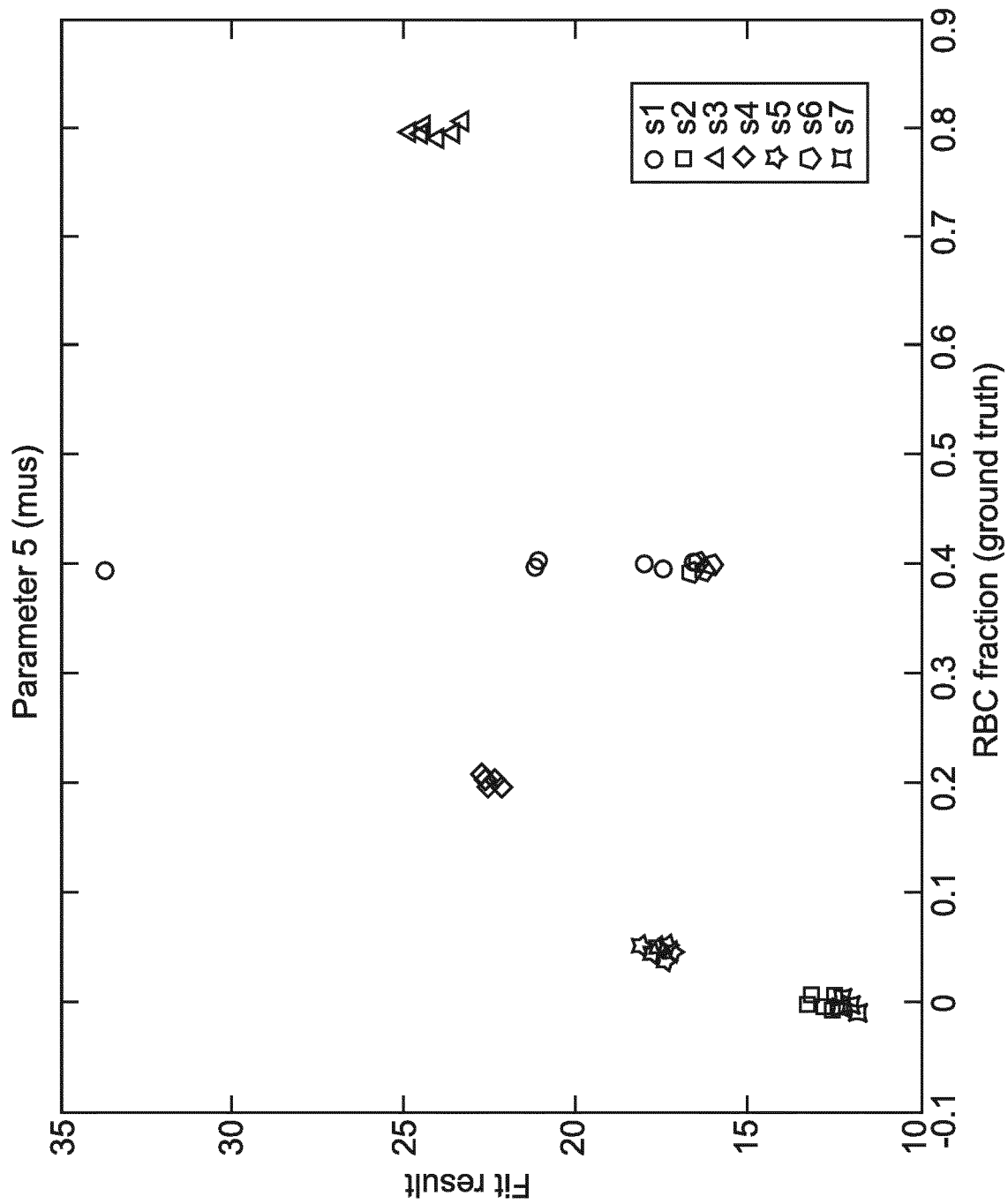

FIG. 9 shows a relationship between the Red Blood Cell concentration in blood clot samples (x-axis) and the fitted scattering at 800 nm (y-axis) for blood clot samples of various composition. It is to be noted that ccattering is a complex behavior that is described by multiple parameters, so other scattering parameters may need to be taken into account as well.

Figure 10:
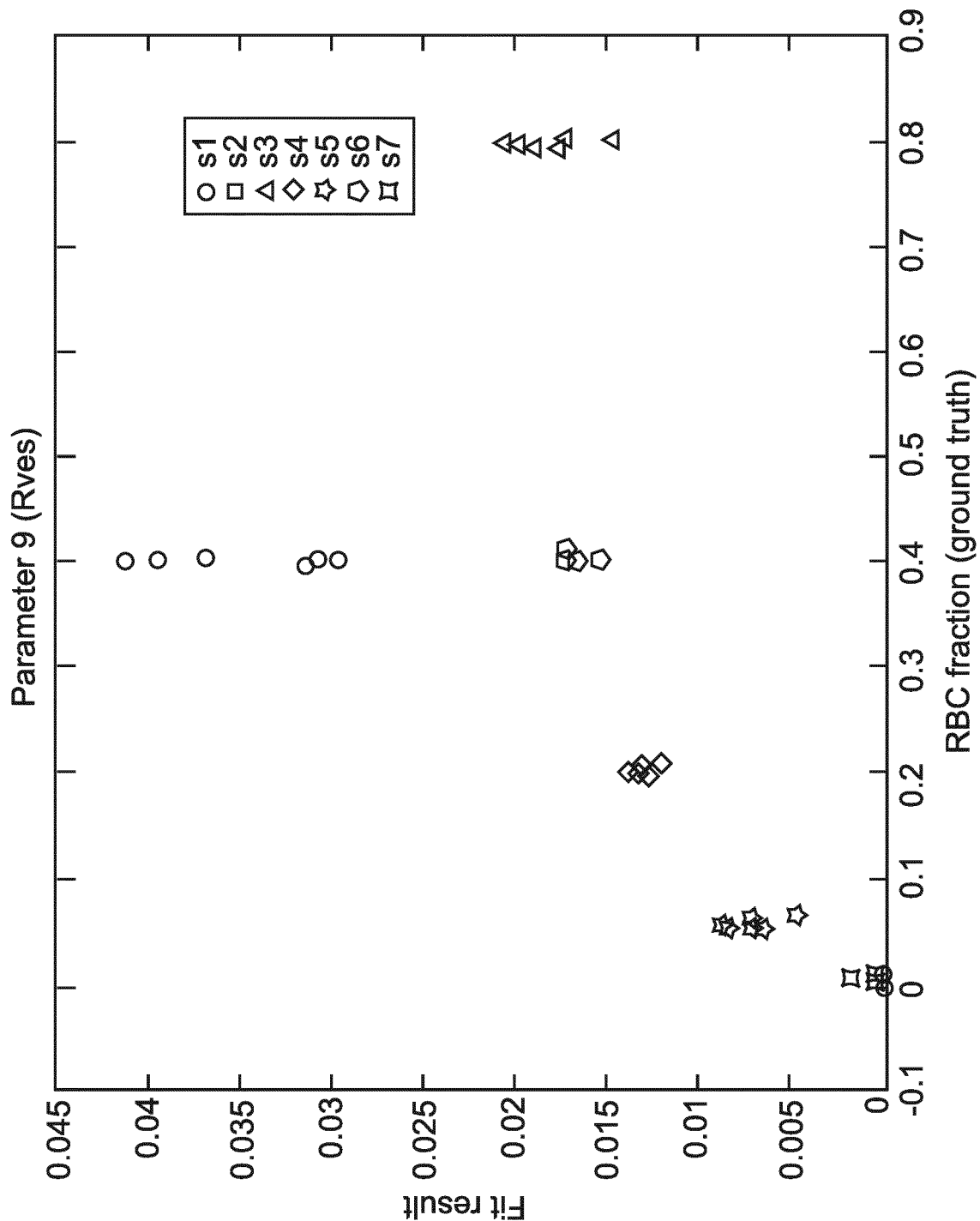

FIG. 10 shows a relationship between the Red Blood Cell concentration in blood clot samples (x-axis) and the fitted vessel radius parameter (y-axis) for blood clot samples of various composition. Si is an inhomogeneous sample which has areas of higher and lower red blood cell concentration.

Figure 11:
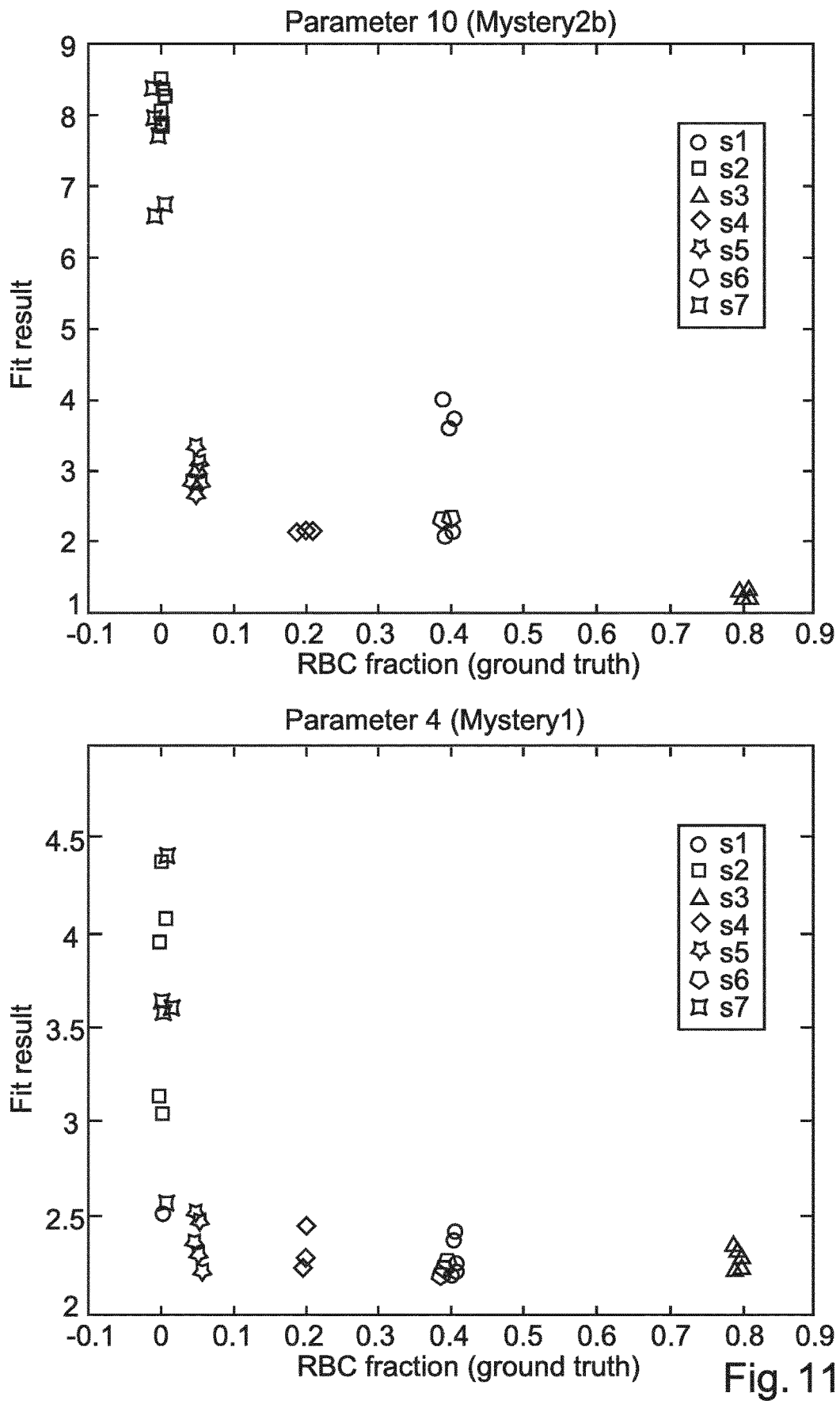

FIG. 11 shows a relationship between the Red Blood Cell concentration in blood clot samples (x-axis) and the fitted concentration of the two unidentified absorbers (y-axis), with the top plot for an absorber around 1380 nm and the bottom plot for an absorber around 1180 nm. This shows the concentration of the unknown chromophore(s) that is responsible for the absorption at 1180 nm and 1380 nm, and correlates inversely with the concentration of red blood cells in the blood clots (and therefore correlates with the concentration of fibrin in the blood clots).

FIGS. 6-11 show how various fit parameters (total hemoglobin and methemoglobin concentration, scattering and the vessel radius parameter) correlate with the ground truth for the samples that are measured. This demonstrates that these fit parameters can be used to determine blood clot composition.

Figure 12:
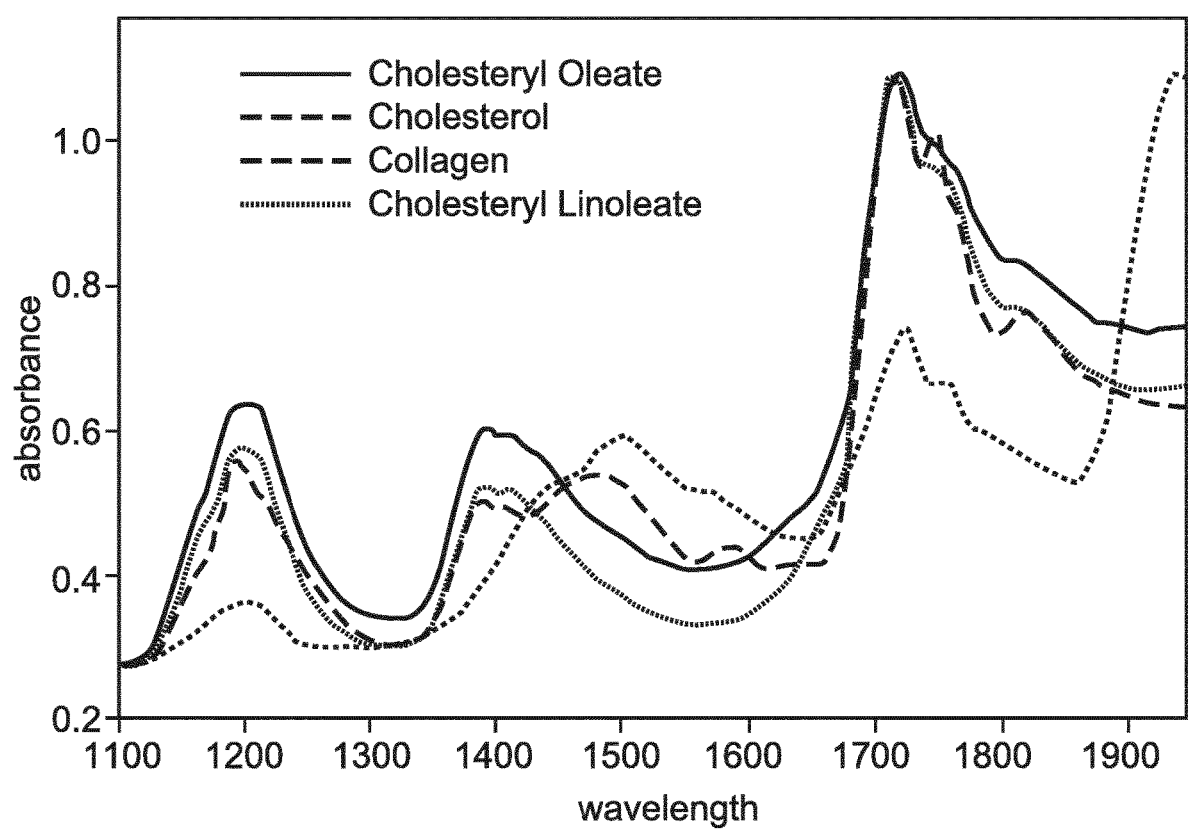
FIG. 12 shows the absorption curves of Cholesterol and related substances, with Cholesterol exhibiting strong absorption features around 1180 nm and 1380 nm.

It is to be noted for the specific case discussed above, absorption curves of the unknown chromophores can be replaced with the absorption of cholesterol which also exhibits strong absorption features around 1180 nm and 1380 nm, as shown in FIG. 12. The absorption curves of the unknown chromophores can also be (partly) replaced with the absorption of elastin which also exhibits a strong absorption feature around 1180 nm. Further information on elastin, including absorption curve information, can be found in US2013/0245616A1.

The above, in part, has been described with respect to unknown absorbers at 1180 nm and 1380 nm, however the above can also be carried out for unknown absorbers at other wavelengths.

SUMMARY

In summary, a detailed example of a system for determining information relating to a blood clot consists of:

A guidewire suitable for neurological use;
that contains optical fibers, preferably a single optical fiber, that
guides white light (preferably including light of a wavelength between 300 nm and 800 nm) to the tip of the guide wire and reflected light from the tip of the guide wire to a console;
the console contains:
a spectrally resolving element, such a spectrometer;
a processing unit that evaluates the spectrum; and
an output unit that, based on the result of the evaluation, displays whether a clot has been detected in front of the wire;
if a blood clot has been detected:
the type of blood clot is determined and output to the physician;
a suggestion or an evaluation of which thrombectomy devices are most suitable for the removal of the clot is provided and output, or it is determined that the clot should be treated with thrombolysis;
and/or an assessment of the physical consistency or density of the clot;
and or an assessment of the fibrin content of the clot
a reference measurement of blood can be made in the neighborhood of the clot, which is used as a base reference to which the measurement of the clot is compared. In this way the natural occurring variations in blood composition between patients is accounted for leading to a more robust discrimination signal.

In summary, a another detailed example of a system for determining information relating to a blood clot consists of:
A guidewire suitable for neurological use;
that contains optical fibers, preferably a single optical fiber, that
guides white light (preferably including light of a wavelength between 1100 nm and 1500 nm) to the tip of the guide wire and reflected light from the tip of the guide wire to a console;
the console contains:
a spectrally resolving element, such a spectrometer;
a processing unit that evaluates the spectrum and determines one or more location dependent parameter(s);
the processing unit runs an algorithm that determines absorption at around 1180 nm and/or 1380 nm; and
an output unit that, based on the result of the evaluation, displays whether a clot has been detected in front of the wire;
if a blood clot has been detected:
the type of blood clot is determined and output to the physician;
a suggestion or an evaluation of which thrombectomy devices are most suitable for the removal of the clot is provided and output, or it is determined that the clot should be treated with thrombolysis;
and/or an assessment of the physical consistency or density of the clot;
and or an assessment of the fibrin content of the clot
a reference measurement of blood can be made in the neighborhood of the clot, which is used as a base reference to which the measurement of the clot is compared. In this way the natural occurring variations in blood composition between patients is accounted for leading to a more robust discrimination signal.

In another exemplary embodiment, a computer program or computer program element is provided that is characterized by being configured to execute the method steps of the method according to one of the preceding embodiments, on an appropriate system.

The computer program element might therefore be stored on a computer unit, which might also be part of an embodiment. This computing unit may be configured to perform or induce performing of the steps of the method described above. Moreover, it may be configured to operate the components of the above described apparatus and/or system. The computing unit can be configured to operate automatically and/or to execute the orders of a user. A computer program may be loaded into a working memory of a data processor. The data processor may thus be equipped to carry out the method according to one of the preceding embodiments. The computer program or the output unit may be integrated into an imaging or a navigation system.

This exemplary embodiment of the invention covers both, a computer program that right from the beginning uses the invention and computer program that by means of an update turns an existing program into a program that uses invention.

Further on, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A system for determining information relating to an occluding structure, comprising:
    at least one optical fiber configured to:
        transfer broadband radiation generated by a broadband radiation source to within a vascular structure, and
        transfer a measurement of at least one broadband radiation reflected from within the vascular structure,
        wherein the at least one broadband radiation comprises a first broadband radiation acquired from a region of interest within the vascular structure, wherein an occluding structure is located within the region of interest and the first broadband radiation is associated with the occluding structure, wherein the first broadband radiation comprises radiation reflected from the formed occluding structure, and wherein the at least one broadband radiation comprises a second broadband radiation that comprises radiation reflected from blood or a vessel wall located near the formed occluding structure within the vascular structure;
    a spectral resolving device configured to provide at least one spectrally resolved data set, the spectral resolving device being a wavelength resolving device configure to determine the at least one spectrally resolved data set, the at least one spectrally resolved data set comprising a first spectrally resolved data set, including a spectrum of the formed occluding structure, determined based on the first broadband radiation and a second spectrally resolved data set, including a spectrum of the blood or the vessel wall located near the formed occluding structure, determined based on the second broadband radiation;
    a processor configured to:
        receive the first spectrally resolved data set and the second spectrally resolved data set,
        identify the formed occluding structure in the vascular structure,
        detect whether the formed occluding structure is a blood clot based on comparing (i) the spectrum of the formed occluding structure to (ii) the spectrum of the blood or the vessel wall located near the formed occluding structure, and
        determine information relating to the occluding structure, including type of the blood clot if the occluding structure is the blood clot, based on determination of a ratio between (i) the spectrum of the occluding structure and (ii) the spectrum of the blood or the vessel wall located near the occluding structure; and
    an output unit configured to output the information relating to the occluding structure.

2. The system according to claim 1, wherein the second broadband radiation is reflected from the region of interest.

3. The system according to claim 1, wherein the occluding structure is the blood clot and determination of the information relating to the blood clot comprises a differentiation between a first blood clot type that is rich in red blood cells and a second blood clot type that is rich in fibrin.

4. The system according to claim 3, wherein the differentiation between the first blood clot type and the second blood clot type comprises a determination of at least one physiological parameter comprising one or more of: amount of haemoglobin; haemoglobin oxygen saturation; an amount of scattering; a vessel packaging parameter; water content; and the amount of at least one haemoglobin derivative.

5. The system according to claim 4, wherein the determination of the at least one physiological parameter comprises one or more of: a fitting of an optical model to the at least one spectrally resolved data set; application of at least one multivariate analysis tool to the at least one spectrally resolved data set; a partial least squares discriminant analysis of the at least one spectrally resolved data set; application of support vector machines to the at least one spectrally resolved data set; application of a k nearest neighbor analysis; and application of deep learning algorithms to the at least one spectrally resolved data set.

6. The system according to claim 4, wherein the differentiation between the first blood clot type and the second blood clot type comprises utilization of a look-up-table.

7. The system according to claim 1, wherein the at least one broadband radiation comprises radiation in the range 400 nm to 800 nm.

8. The system according to claim 1, wherein the occluding structure is the blood clot and the information relating to the blood clot comprises one or more of: an evaluation of which thrombectomy device or devices is or are most suitable for removal of the blood clot; an assessment of the physical consistency of the blood clot; an assessment of the density of the blood clot; and an assessment of the fibrin content of the blood clot.

9. A method for determining information relating to an occluding structure, comprising:
    identifying an occluding structure formed within a vascular structure;

positioning at least one optical fiber to transfer broadband radiation toward the formed occluding structure and measuring a first broadband radiation reflected from the formed occluding structure;

positioning the at least one optical fiber to transfer broadband radiation away from the occluding structure and toward blood or a vessel wall located near the formed occluding structure and measuring a second broadband radiation reflected from the blood or the vessel wall located near the formed occluding structure;

determining at least one spectrally resolved data set, wherein the at least one spectrally resolved data set comprising a first spectrally resolved data set, including a spectrum of the formed occluding structure, determined based on the first broadband radiation and a second spectrally resolved data set, including a spectrum of the blood or the vessel wall located near the formed occluding structure, determined based on the second broadband radiation;

providing the first spectrally resolved data set and the second spectrally resolved data set;

detecting whether the occluding structure is a blood clot based on comparing (i) the spectrum of the formed occluding structure to (ii) the spectrum of the blood or the vessel wall located near the formed occluding structure;

determining information relating to the occluding structure, including type of the blood clot if the occluding structure is the blood clot, based on determination of a ratio between ci) the spectrum of the occluding structure and (ii) the spectrum of the blood or the vessel wall located near the occluding structure; and outputting the information relating to the occluding structure.

10. The method according to claim 9, wherein the second broadband radiation is reflected from the region of interest.

11. The method according to claim 9, wherein the occluding structure is the blood clot and determination of the information relating to the blood clot comprises a differentiation between a first blood clot type that is rich in red blood cells and a second blood clot type that is rich in fibrin.

12. The method according to claim 11, wherein the differentiation between the first blood clot type and the second blood clot type comprises a determination of at least one physiological parameter comprising one or more of: amount of haemoglobin; haemoglobin oxygen saturation; an amount of scattering; a vessel packaging parameter; water content; and the amount of at least one haemoglobin derivative.

13. The method according to claim 12, wherein the determination of the at least one physiological parameter comprises one or more of: a fitting of an optical model to the at least one spectrally resolved data set; application of at least one multivariate analysis tool to the at least one spectrally resolved data set; a partial least squares discriminant analysis of the at least one spectrally resolved data set; application of support vector machines to the at least one spectrally resolved data set; application of a k nearest neighbor analysis; and application of deep learning algorithms to the at least one spectrally resolved data set.

14. The method according to claim 9, wherein the occluding structure is the blood clot and the information relating to the blood clot comprises one or more of: an evaluation of which thrombectomy device or devices is or are most suitable for removal of the blood clot; an assessment of the physical consistency of the blood clot; an assessment of the density of the blood clot; and an assessment of the fibrin content of the blood clot.

15. A non-transitory computer-readable storage medium having stored a computer program comprising instructions which, when executed by a processor, cause the processor to:

identify an occluding structure formed within a vascular structure;

transfer, by at least one optical fiber, broadband radiation toward the occluding structure formed within a vascular structure and measure a first broadband radiation reflected from the occluding structure;

transfer, by the at least one optical fiber, the broadband radiation away from the occluding structure and toward blood or a vessel wall located near the occluding structure and measure a second broadband radiation reflected from the blood or a vessel wall located near the occluding structure;

determine at least one spectrally resolved data set, wherein the at least one spectrally resolved data set comprises a first spectrally resolved data set, including a spectrum of the formed occluding structure, determined based on the first broadband radiation and a second spectrally resolved data set, including a spectrum of the blood or the vessel wall located near the formed occluding structure, determined based on the second broadband radiation;

provide the first spectrally resolved data set and the second spectrally resolved data set;

detect whether the occluding structure is a blood clot based on comparing (i) the spectrum of the formed occluding structure to (ii) the spectrum of the blood or the vessel wall located near the formed occluding structure;

determine information relating to the suspected occluding structure, including type of the blood clot if the occluding structure is the blood clot, based on a ratio between ci) the spectrum of the occluding structure and (ii) the spectrum of the blood or the vessel wall located near the occluding structure; and output the information relating to the occluding structure.

16. The non-transitory computer-readable storage medium according to claim 15, wherein the second broadband radiation is reflected from the region of interest.

17. The non-transitory computer-readable storage medium according to claim 15, wherein the occluding structure is the blood clot and determination of the information relating to the blood clot comprises a differentiation between a first blood clot type that is rich in red blood cells and a second blood clot type that is rich in fibrin.

18. The non-transitory computer-readable storage medium according to claim 17, wherein the differentiation between the first blood clot type and the second blood clot type comprises a determination of at least one physiological parameter comprising one or more of: amount of haemoglobin; haemoglobin oxygen saturation; an amount of scattering; a vessel packaging parameter; water content; and the amount of at least one haemoglobin derivative.

19. The non-transitory computer-readable storage medium according to claim 18, wherein the determination of the at least one physiological parameter comprises one or more of: a fitting of an optical model to the at least one spectrally resolved data set; application of at least one multivariate analysis tool to the at least one spectrally resolved data set; a partial least squares discriminant analysis of the at least one spectrally resolved data set; application of support vector machines to the at least one spectrally resolved data set; application of a k nearest neighbor analysis; and application of deep learning algorithms to the at least one spectrally resolved data set.

20. The non-transitory computer-readable storage medium according to claim 15, wherein the occluding structure is the blood clot and the information relating to the blood clot comprises one or more of: an evaluation of which thrombectomy device or devices is or are most suitable for removal of the blood clot; an assessment of the physical consistency of the blood clot; an assessment of the density of the blood clot; and an assessment of the fibrin content of the blood clot.

* * * * *